United States Patent
Warnecke

(10) Patent No.: US 6,533,112 B2
(45) Date of Patent: Mar. 18, 2003

(54) PACKAGING FOR SURGICAL SUTURE MATERIAL

(75) Inventor: Henning Warnecke, Hamburg (DE)

(73) Assignee: Ethicon, GmbH (DE)

( * ) Notice: Subject to any disclaimer, the term of this patent is extended or adjusted under 35 U.S.C. 154(b) by 0 days.

(21) Appl. No.: 09/727,918

(22) Filed: Dec. 1, 2000

(65) Prior Publication Data
US 2001/0004966 A1 Jun. 28, 2001

(30) Foreign Application Priority Data
Dec. 3, 1999 (DE) .......................... 199 59 263

(51) Int. Cl.⁷ .............................................. A61B 17/06
(52) U.S. Cl. ........................ 206/63.3; 206/380; 206/482
(58) Field of Search ............................. 206/63.3, 480, 206/225, 388, 482, 380, 339, 227

(56) References Cited

U.S. PATENT DOCUMENTS

| | | | |
|---|---|---|---|
| 3,768,635 A | * 10/1973 | Eggert | 206/380 |
| 4,619,364 A | * 10/1986 | Czopor, Jr. | 206/379 |
| 5,335,783 A | 8/1994 | Hans-Jurgen | |
| 5,675,961 A | 10/1997 | Cerwin et al. | |
| 5,704,469 A | * 1/1998 | Daniele et al. | 206/63.3 |
| 5,733,293 A | * 3/1998 | Scirica et al. | 206/63.3 |
| 5,833,055 A | * 11/1998 | Cerwin et al. | 206/63.3 |
| 6,016,905 A | * 1/2000 | Gemma et al. | 206/63.3 |
| 6,047,815 A | * 4/2000 | Cerwin et al. | 206/63.3 |
| 6,076,659 A | * 6/2000 | Baumgartner et al. | 206/63.3 |

FOREIGN PATENT DOCUMENTS

| | | |
|---|---|---|
| EP | 168172 | 1/1986 |
| EP | 0471458 | 7/1991 |
| EP | 471458 | 2/1992 |
| EP | 941699 | 9/1999 |
| GB | 1118819 | 7/1968 |

OTHER PUBLICATIONS

EPO Search Report 0125260, Jan. 17, 2002.

* cited by examiner

Primary Examiner—Shian Luong
(74) Attorney, Agent, or Firm—Emil Richard Skula

(57) ABSTRACT

In a packaging (1) for surgical suture material, a thread duct (10) which runs in a wound manner is formed in a base (2), which thread duct opens at its first end (11) to a thread removal zone (3). The base (2) is provided with a cover. The thread removal zone (3) has a recess (24) in the base (2) adjacent to the first end (11) of the thread duct (10), adjacent to which recess a thread tray (26), which faces the first end (11) of the thread duct (10), is located.

51 Claims, 6 Drawing Sheets

PACKAGING FOR SURGICAL SUTURE MATERIAL

TECHNICAL FIELD

The invention relates to a packaging for surgical suture material, with a base in which a thread duct which runs in a wound manner is formed, which opens at its first end to a thread removal zone, and with a cover for the base.

BACKGROUND OF THE INVENTION

Such packagings for surgical suture material are known and described e.g. in EP 0 471 458 A1. At least one surgical thread can be housed in the thread duct, which can be removed from the packaging via the thread removal zone, which is arranged here in the periphery area of the base, after opening the packaging. Being guided through the thread duct is to prevent the surgical thread from sticking or becoming entangled with other thread parts. As the thread duct is constructed in a wound manner (e.g. in a spiral-like manner), relatively long surgical threads can be housed in a compact packaging.

In the packaging for surgical suture material known from EP 0 471 458 A1, there is located at the thread removal zone in the cover an opening through which a surgical needle projects which is attached to the end of a surgical thread stored in the packaging. To remove the suture material, it is necessary to pull on the needle. The thread then slides through the relatively small opening and can rub against the edge of the opening, which is a disadvantage. A further disadvantage of the previously known packaging is that the front end of the thread, here in the area of the point of attachment to the needle, must be guided through the opening in the cover with a fairly small radius of curvature as the front end area of the thread or the needle is otherwise not safely accessible after the packaging is opened (which is carried out by folding down a flap covering the opening away from the cover). In areas with a small radius of curvature or at kinks, a surgical thread does not generally reassume its original straight form again after removal from the packaging (thread memory effect), which is not desired.

SUMMARY OF THE INVENTION

The object of the invention is to provide a packaging for surgical suture material from which surgical suture material can be removed easily and without problems, a thread memory effect being largely avoided.

This object is achieved by a packaging for surgical suture material with the features of claim 1. Advantageous versions of the invention result from the dependent claims.

The packaging according to the invention for surgical suture material has a base in which a thread duct running in a wound manner is formed. The thread duct opens at one end, its first end, to a thread removal zone which is preferably formed in the peripheral area of the base. The packaging also has a cover for the base. The thread removal zone has a recess in the base which is adjacent to the first end of the thread duct. A thread tray facing the first end of the thread duct is located adjacent to this recess.

The packaging according to the invention is particularly suitable for needleless suture material, i.e. for surgical threads to which no surgical needle is attached; it can however also be used for suture material with needles. The thread duct can serve to house one, but also several surgical threads. The front end areas of the surgical threads (to which a needle is optionally attached) project out of the first end of the thread duct, bridge the recess of the thread removal zone and end (optionally with the needle) on the thread tray.

To remove the surgical suture material from the packaging according to the invention, a gastight sealed outer wrapper generally provided is firstly opened and the packaging removed from it. The thread removal zone is immediately accessible; it is not necessary to open an additional locking piece. A surgeon or an assistant can therefore grip the surgical threads in the area of the recess without any problems and pull them from the thread tray. The free ends of the surgical threads (or optionally the needles) fan out slightly so that a desired thread can be removed safely and quickly.

The removal of the suture material is particularly easy if the recess of the thread removal zone extends from the periphery of the base, i.e. if it is freely accessible from the periphery of the base, as is the case in a preferred version.

The surgical suture material need not be guided through a relatively narrow opening in the cover, as with the packaging known from EP 0 471 458 A1, but can be pulled directly from the first end of the thread duct via the freely accessible thread removal zone. Surgical suture material located in the packaging can be laid so that no undesired kinks form. To avoid a thread memory effect, it is also advantageous to have the thread removal zone preferably situated in the peripheral area of the base, as the initially more closely wound coils of a surgical thread which are located in the inner area of the packaging when packed are extended to ever-greater radii of curvature when pulled out through the thread duct.

In a preferred version of the invention, the thread tray is arranged in the base, and preferably as a part of the bottom of the base. A thread holder is preferably located above the thread tray, which can have a nose which extends from a raised edge of the base. In this case, the front end of the surgical threads (or optionally the needles attached to them or their tips) are held particularly safely and protected in the packaging. The thread holder can be located directly above the thread tray, or (e.g. for manufacturing reasons) displaced with respect to the thread tray.

The cover preferably leaves the thread removal zone free or essentially free, i.e. the cover does not cover the thread removal zone. The end areas of the surgical threads (or optionally the needles attached to them) are therefore directly visible, which facilitates the removal of the threads individually or also in bundles.

If the cover partly or completely covers the thread removal zone, then the thread holder can be formed by a part of the cover.

In a preferred design of the invention, the base has a raised edge in the area of the thread tray. This raised edge preferably runs transverse to the axis of the thread duct, which extends in the longitudinal direction of the thread duct in the area of the first end of the thread duct. This means that this axis determines the direction in which a surgical thread emerges from the thread duct. As the raised edge runs transverse to this in the area of the thread tray, the surgical threads have a curvature in the area between the first end of the thread duct and the thread tray, so that the end areas of the surgical threads are somewhat pressed against the raised wall, which ensures a particularly safe hold.

The thread duct is preferably formed in spiral-like manner. This makes it possible to house one or more relatively long surgical threads on a relatively small surface area of the base. In a version with a spiral-like thread duct, the second end of the thread duct is located proximate a peripheral edge of the base. In another version with a spiral-like thread duct, the thread duct has a turn in the central area of the base and is led back to the peripheral area of the base where the second end of the thread duct is located.

In a preferred design of the invention, the base and/or the cover has an opening in the area of the second end of the thread duct. To fill the packaging with surgical suture material, below-atmospheric pressure can be applied to this opening. In this way, surgical threads, which are introduced into the first end of the thread duct with their ends opposite the ends considered up to now, can be sucked into the thread duct without problems.

The cover is preferably designed as a flat sheet and can comprise cardboard or paper (preferably paper of medical quality). The cover preferably has polyethylene or polypropylene or a spunbonded polyolefine (such as e.g. polyolefine fibre tissue (fleece) sold by DuPont under the mark "Tyvek") on its underside facing the base. The cover can for example consist of a sheet or film made from polyethylene or polypropylene or a sheet made from "Tyvek", but composite structures containing cardboard or paper are also conceivable. In a particularly advantageous version of the invention, the cover is made from a piece of cardboard which is coated on its underside with polyethylene. Such a cover has various advantages: Cardboard is suitable for imprinting, so that the packaging can be easily provided with a product label. Furthermore, cardboard acts as a hydrostore, i.e. it is able to absorb residual quantities of water after a packaging with surgical suture material has been introduced into a tight outer wrapper. The cover covers the thread duct at the top and thus protects the surgical suture material contained in it. Such a cover acts as a lid for the base and thus reinforces the entire package. Furthermore, the paper fibres of the cardboard are bound by the polyethylene coating on the side of the cover facing the surgical suture material so that no contamination of the product contained in the packaging can occur. In principle, the cover can be glued onto the base e.g. with dispersion varnish or adhesive, but it is sealed in the particularly advantageous version (see below).

The base is preferably formed as an injection-molded part and can consist of polyethylene or polypropylene. Injection-molded parts can be prepared in large quantities at favorable cost and with high precision.

In the particularly advantageous version mentioned, the cover is sealed onto the base which is made from polyethylene in this case. To do this, the cover or the base or both components are heated so that the two facing surfaces containing polyethylene melt together. The temperature and the contact pressure are preferably chosen so that a bead forms to the cover in the upper end area of the thread duct wall. This bead forms from surplus melted polyethylene which is pulled from the duct wall in a furrow-like manner to the polyethylene coating on the underside of the cover as a result of intermolecular interactions. The bead formation has the advantage that gaps are reliably avoided between the upper end area of the duct wall and the cover. Therefore there is no need to fear that when surgical suture material is removed, a thread becomes stuck or pulled tight in such a gap, which would be a great disadvantage. The particularly advantageous version of the packaging according to the invention for surgical suture material can be cheaply produced and also has a cross-section form of the thread duct which enables the thread to be withdrawn safely.

To avoid the base warping when the cover is sealed on, a basis sheet is sealed onto the underside of the base in a preferred version. The basis sheet can be formed in the same way as the cover, thus for example it can be made from cardboard coated with polyethylene, the polyethylene facing the underside of the base. The cover and the base sheet are preferably sealed on simultaneously. When cooling, the tensions on the top and on the underside of the base compensate largely so that the packaging does not warp or bend, or only slightly.

The packaging according to the invention for surgical suture material can thus be produced cheaply and is simple and reliable in handling. In particular, the surgical threads contained in the packaging (optionally threads with needles) can be removed individually or in bundles easily and without problems, as the thread removal zone is directly accessible. When removing the surgical suture material, the threads are at most minimally damaged, as they are neither squeezed nor squashed nor sharply bent. The packaging can be produced with small dimensions and a small overall height, although it is suitable for storing relatively long surgical threads. This reduces the storage and transport costs. Packagings, which are similarly constructed in principle, can be used for completely different thread lengths and also thread numbers.

BRIEF DESCRIPTION OF THE DRAWINGS

In the following, the invention is explained in more detail by means of embodiments. The diagrams show in FIG. 1 a perspective view of a version of a packaging according to the invention for surgical suture material which contains surgical threads, FIG. 2 a perspective view of the packaging for surgical suture material from FIG. 1, the cover and the surgical threads being removed.

DESCRIPTION OF PREFERRED EMBODIMENTS

Figure 1:
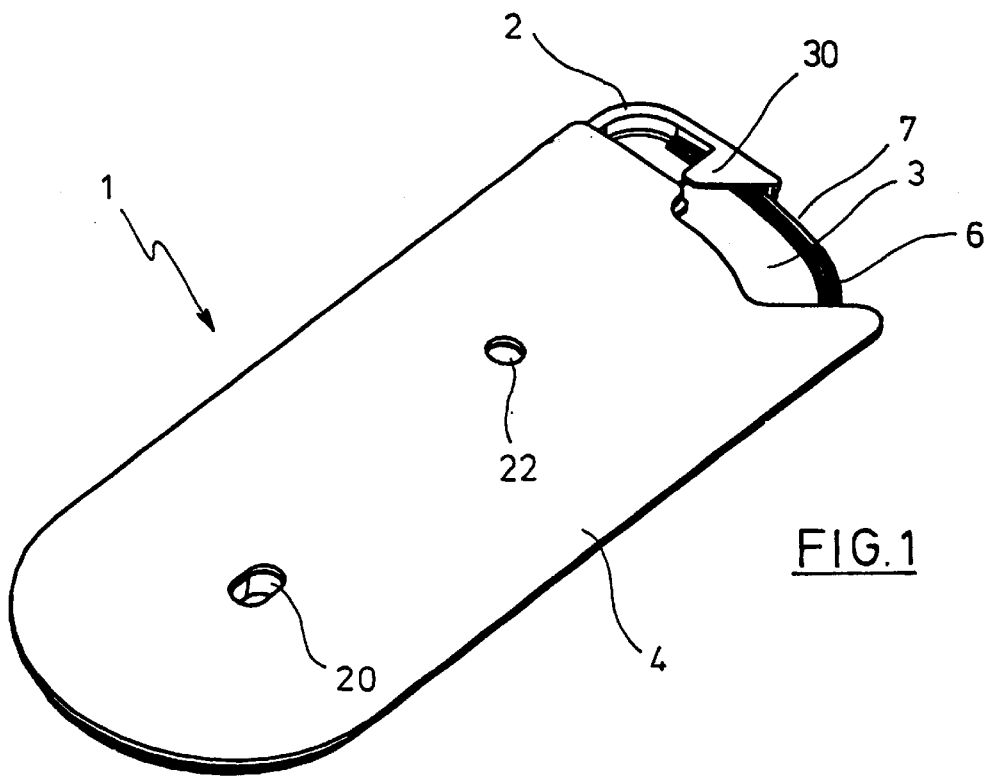

A first version of a packaging 1 for surgical suture material is shown in FIG. 1 in perspective view. The packaging 1 has a base 2, which is provided with a thread removal zone 3 in a peripheral area. In the embodiment, the thread removal zone 3 is located at an end side of the packaging 1. A thread duct which runs in a wound manner is arranged in the base 2 (see FIG. 2 and FIG. 3). A cover 4 is located above the base 2. A plurality of surgical threads 6 is housed in the packaging 1, which are needleless in the embodiment, but which can also be provided with surgical needles. The end areas 7 of the threads 6 projecting from the thread duct are held in the thread removal zone 3, as is shown in FIG. 1. It is described in more detail below how the threads 6 can be removed from the packaging 1.

The base 2 is formed in the embodiment in one piece as an injection-molded part and is composed of polyethylene. Other materials, such as e.g. polypropylene are also conceivable.

The cover 4 is made from cardboard in the embodiment and is coated with polyethylene on its underside, i.e. the side facing the base 2. A strong bond between cardboard and polyethylene can be achieved, e.g., by hot-rolling a polyethylene film onto cardboard, the polyethylene softening and penetrating into the pores present in the cardboard.

Figure 2:
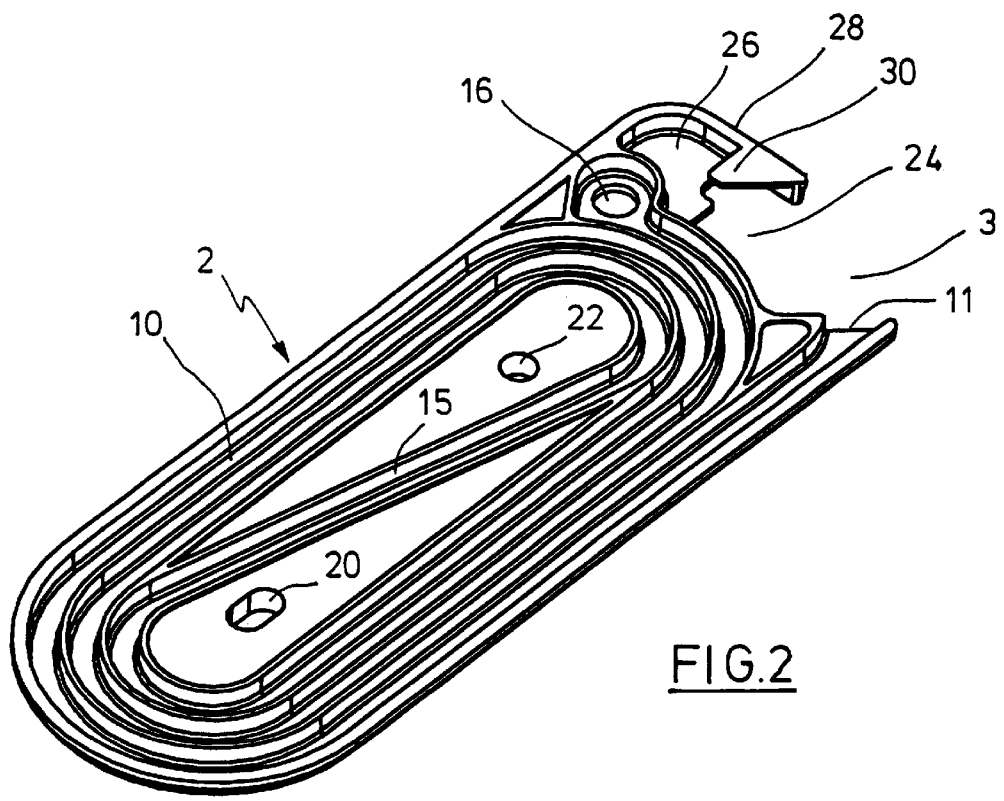
Figure 3:
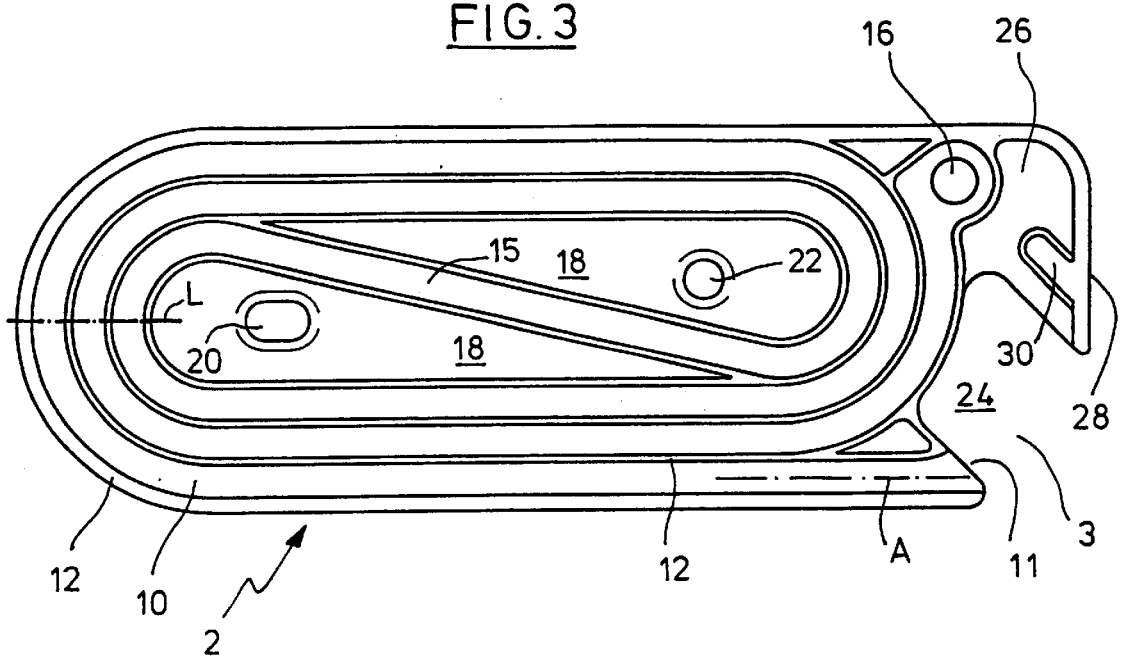
FIG. 3 a top view of the base of a second version of a packaging according to the invention for surgical suture material which differs only slightly from the first version.

The structure of the base 2 is explained in more detail in the following, using FIGS. 2 and 3. FIGS. 2 and 3 relate to different versions of the packaging 1, which differ however only with respect to the thread removal zone 3. Therefore, the same reference numbers are used for both versions.

Figure 5:
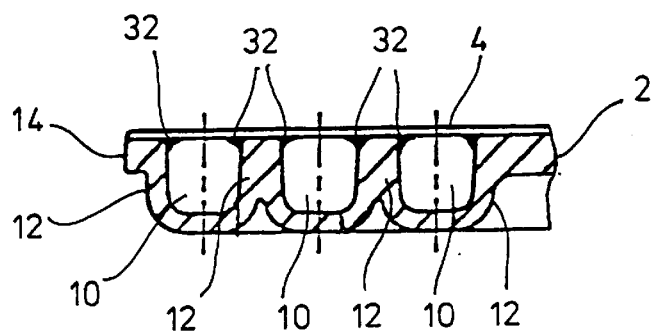
FIG. 5 a longitudinal section through a part of the second version along line L from FIG. 3, FIG. 6 a top view of the second version, the end areas of surgical threads being held in the thread removal zone, FIG. 7 a top view of the second version, the end areas of the surgical threads being released, FIG. 8 an exploded view of a further version of a packaging according to the invention for surgical suture material which has a cover and a basis sheet, FIG. 9 a perspective view from above of the version according to FIG. 8, FIG. 10 a perspective view from below of the version according to FIG. 8, FIG. 11 a longitudinal section through a part of the version according to FIG. 8 along line S from FIG. 9, FIG. 12 for comparison, a corresponding longitudinal section through a version which is very similar to the version according to FIG. 3, and FIG. 13 a corresponding longitudinal section through a further version of the packaging according to the invention for surgical suture material.

A thread duct 10 running in a spiral-like wound manner, which is defined by a thread duct wall 12, with a first end 11, is formed in the base 2. The thread duct wall 12 limits the packaging 1 towards the outside, i.e. on its periphery, and in addition separates the individual coils of the thread duct 10 from one another. At the outer periphery of the packaging 1, the thread duct wall 12 has a strengthening edge 14 (see FIG. 5). The thread duct 10 runs in essentially spiral-like manner, turning inwards starting from its first end 11, but having a turn 15 in the central area of the base 2 so that as it progresses, it approaches the periphery of the base 2 again, see in particular FIG. 3. At the other end of the thread duct 10, its second end, an opening 16 is located on the underside of the base 2, see FIG. 3. If a below-atmospheric pressure is applied to the opening 16, surgical threads 6 can be sucked into the packaging 1 (see below).

The middle region of the base 2 is occupied by a two-part cavity 18 which is not connected to the thread duct 10. A guide hole 20 and a positioning hole 22 facilitate the handling of the packaging 1 during manufacture and filling with surgical suture material.

As is shown in FIGS. 2 and 3, the thread duct 10 opens at its first end 11 to the thread removal zone 3. The thread removal zone 3 has a recess 24 in the base 2, which extends from the periphery of the base 2 and reaches on one side up to the first end 11 of the thread duct 10, while the opposite side defines the start of a thread tray 26. As the recess 24 has no edge on the periphery of the base 2, the recess 24 is freely accessible from the periphery of the base 2.

The thread tray 26 is formed as part of the bottom of the base 2. In the view according to FIG. 3, there is a raised edge 28 located above and to the right of the thread tray 26, while the thread tray is bordered on the left by a part of the thread duct wall 12. A thread holder 30 is arranged above the thread tray 26, which is designed in the embodiment as a nose extending from the raised edge 28. The two versions according to FIG. 2 and FIG. 3 differ in the form of this nose 30. In the version according to FIG. 2, the nose 30 is located above the thread tray 26, but still in the area of the recess 24.

On the other hand, in the version according to FIG. 3, the nose 30 is arranged beside the recess 24 and above the thread tray 26. For manufacturing reasons however, the thread tray 26 has an opening directly under the nose 30.

Figure 4:
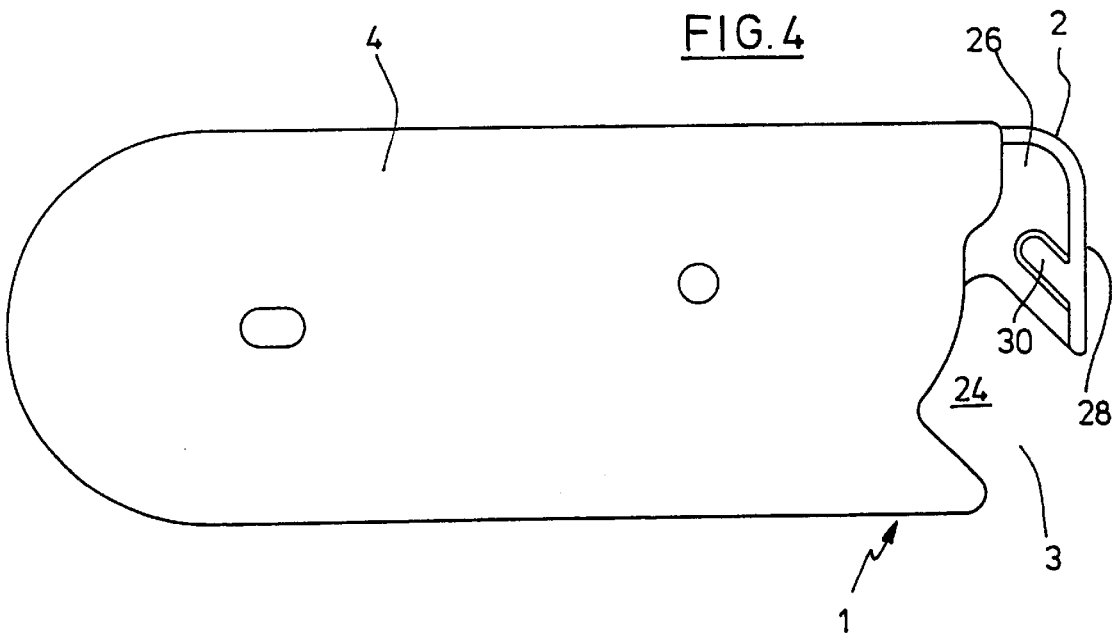
FIG. 4 a top view of the version according to FIG. 3, the cover being attached.
Figure 6:
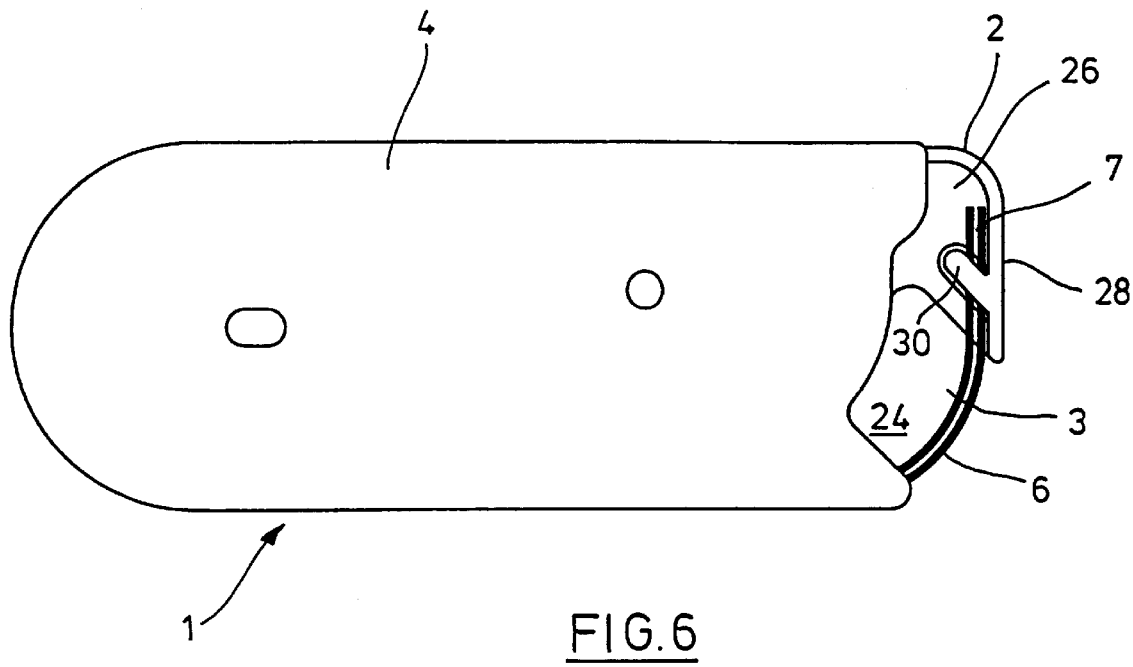

As is shown in FIG. 4, in the embodiment, the cover 4 leaves the thread removal zone 3 exposed so that the end areas 7 of the surgical threads 6 contained in the packaging 1 can be seen, see FIG. 6. The raised edge 28, from which the nose 30 extends, runs transverse to the longitudinal direction of the thread duct 10 marked with A in FIG. 3 in the area of the first end 11 of the thread duct 10. This ensures that the end areas 7 of the threads 6 emerging from the thread duct 10 are bent, see FIG. 6, and lie against the raised edge 28. The end areas 7 are securely held between the thread tray 26 and the nose 30.

In the embodiment, the cover 4 is sealed on the base 2. As the cover 4 is coated with polyethylene on its underside, this polyethylene fuses, when heated, with the polyethylene on the upper side of the thread duct wall 12 of the base 2. In the upper end area of the thread duct wall 12 to the cover 4, beads 32 form, as drawn in black in FIG. 5. These beads prevent a thread 6, which is located inside the thread duct 10, from being pulled into any intermediate space between the base 2 and the cover 4 and sticking there, when it is being pulled out. Thus in the versions described, the cover 4 can be easily secured to the base 2 by being sealed on, which results in a thread duct 10 being closed in cross-section, from which thread removal is possible without problems.

To fill the packaging 1 with surgical suture material, after the cover 4 is secured to the base 2, the surgical threads 6 to be introduced are inserted into the thread duct 10 as a bundle, via the thread removal zone 3, with their ends opposite the end areas 7 introduced at the first end 11 of the thread duct 10. Subsequently, below-atmospheric pressure is applied to the opening 16, through which the surgical threads 6 are sucked into the thread duct 10. After this process is completed, only the end areas 7 project from the thread duct 10. The end areas 7 of the threads 6 are then pushed under the nose 30, so that the position shown in FIG. 6 is achieved.

The packaging 1 is preferably stored in a gastight sealed outer wrapper, which consists of e.g. aluminum foil or an aluminized plastics film. As the glued or sealed seams of such an outer wrapper are not normally absolutely tight, the cardboard used in the embodiment for the cover 4 has the advantage that it absorbs moisture that penetrates these seams over the course of time, and in this way, keeps it away from the suture material. Surgical threads 6, which are manufactured for example from hydrolytically degradable, resorbable material, would lose their strength under the influence of moisture. The cardboard material of the cover 4 has the further advantage that a label for the suture material located in the packaging 1 can be printed on the upper side of the cover 4.

Figure 7:
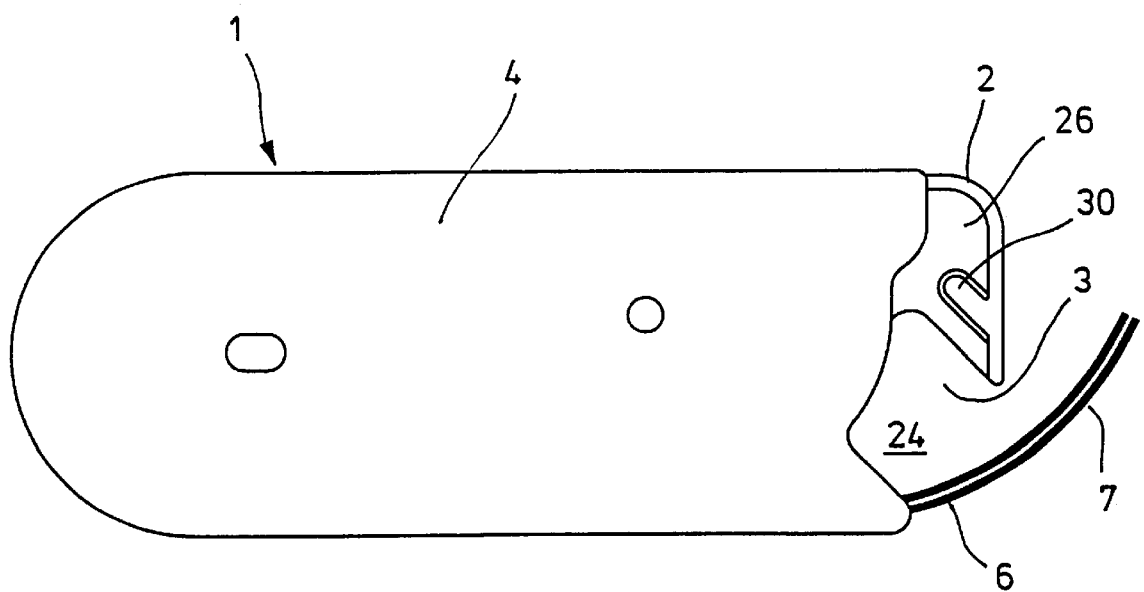

To use the packaging 1, it is firstly removed from the outer wrapper mentioned. The thread removal zone 3 then becomes freely accessible. The surgeon or an assistant can easily grip the end areas 7 of the surgical threads 6 located in the packaging 1 in the area of the recess 24 (e.g. with the help of a pair of tweezers) and either press them slightly inwards, i.e. onto the center of the packaging 1, so that they are released from the holding device formed by the thread tray 26, the raised edge 28 and the nose 30, or move them from this holding device directly by means of an outwardly-directed force. The threads then assume the position shown in FIG. 7. The end areas 7 of the threads 6 fan out slightly so that individual surgical threads 6 can be gripped without problems, and can be removed from the packaging 1. The thread duct 10 running in wound manner guides the surgical threads 6 securely so that they do not becomes entangled or knotted with each other, and when the desired thread is pulled out, the surgical threads 6 remaining in the thread duct 10 are displaced only to a negligible degree.

Figure 8:
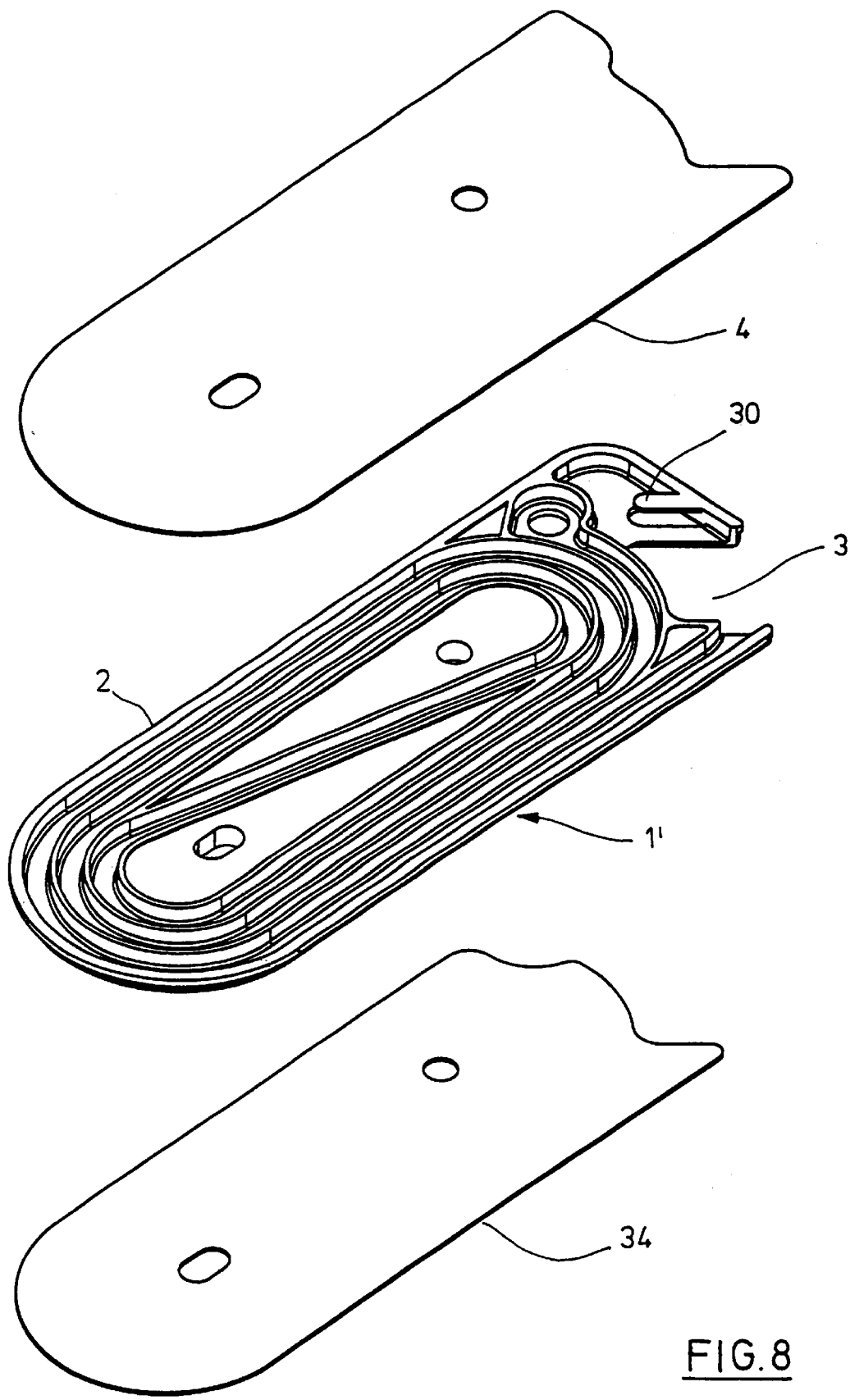

FIG. 8 shows a further version of a packaging 1' for surgical suture material in exploded view. This version largely corresponds to the second version shown in FIGS. 3 to 7, which is why the same reference numbers are used as in the second version. In contrast to this, for the packaging 1', a basis sheet 34 is sealed onto the underside of the base 2, as is also shown in FIGS. 9 and 10.

The basis sheet 34 is preferably constructed exactly like the cover 4. In the embodiment, both the cover 4 and the basis sheet 34 are made of cardboard of 220 g/m$^2$ which is coated with polyethylene on its side facing the base 2. The basis sheet 34 prevents the packaging 1' from warping as a result of tensions occurring during sealing on of the cover 4. The cover 4 and the basis sheet 34 are preferably fused to the base 2 simultaneously and in the same way as previously described.

Figure 9:
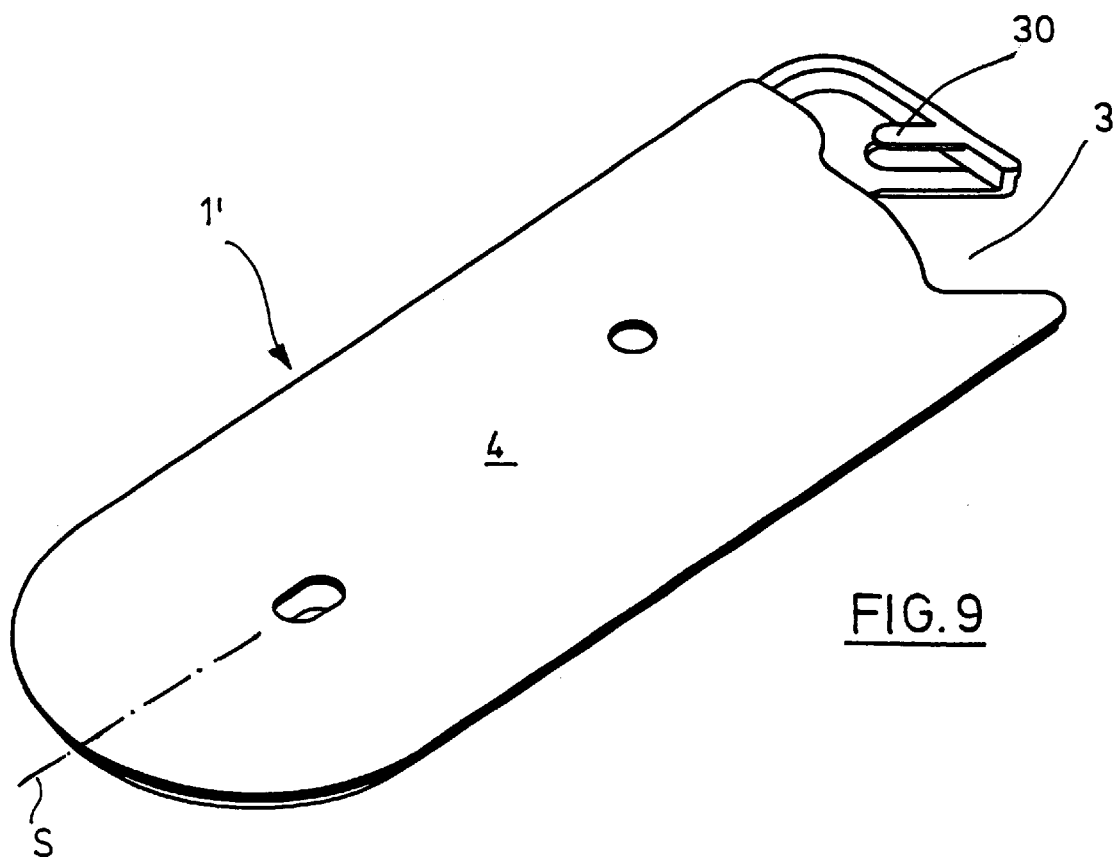
Figure 10:
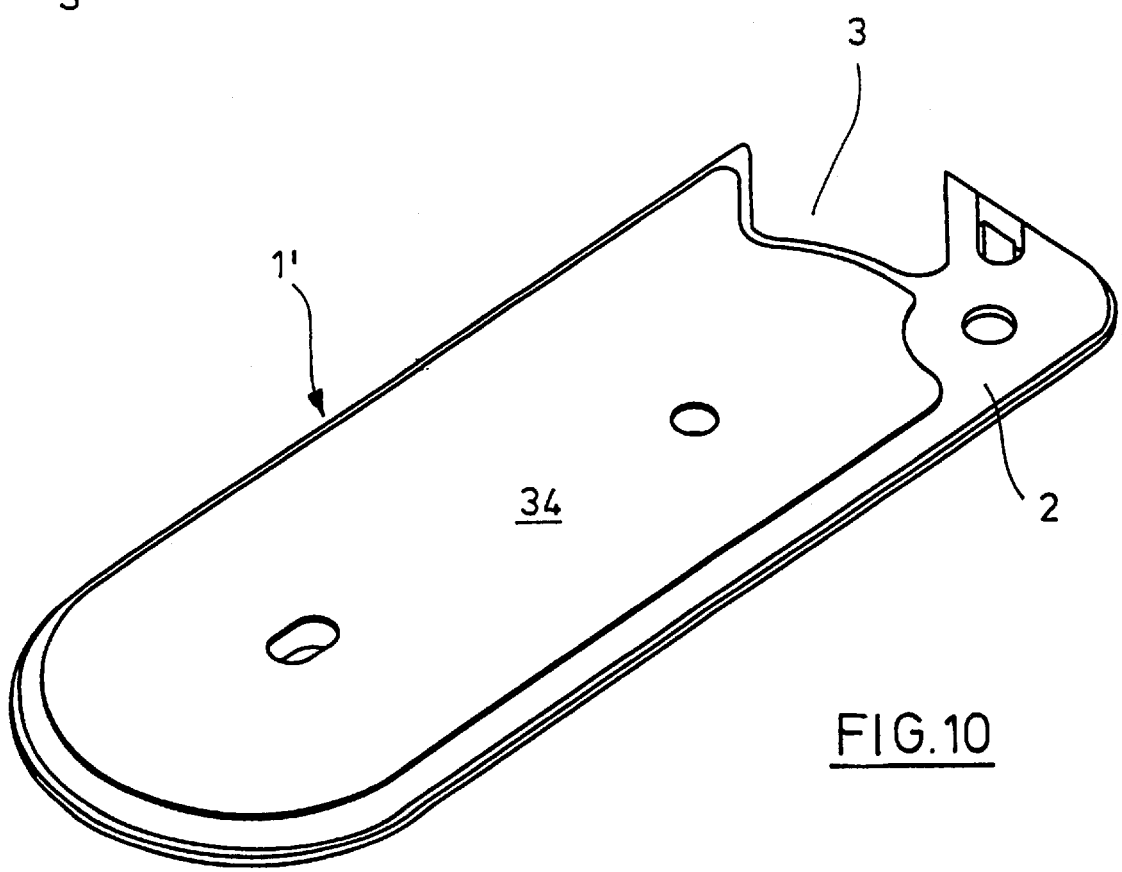
Figure 11:
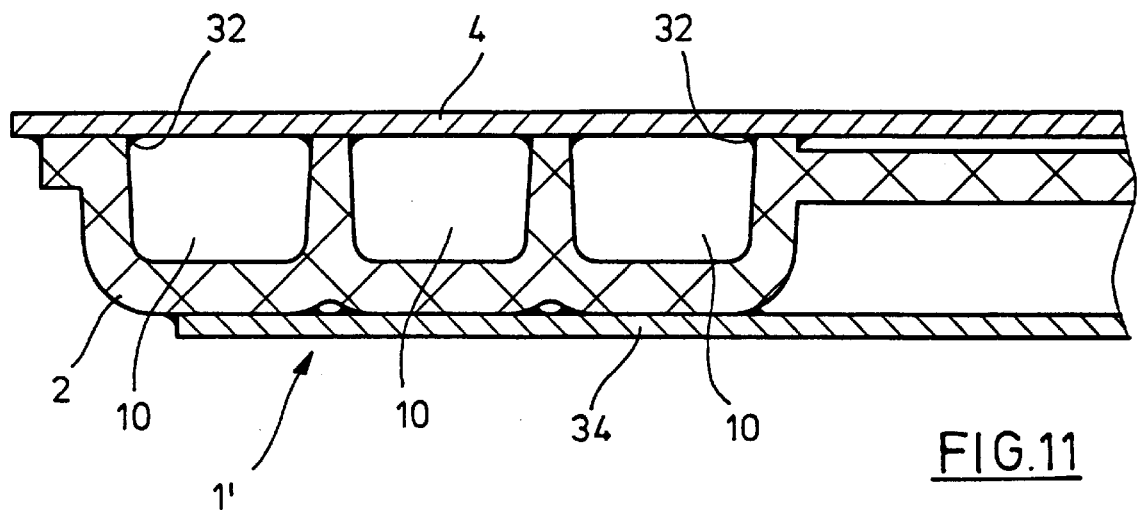
Figure 12:
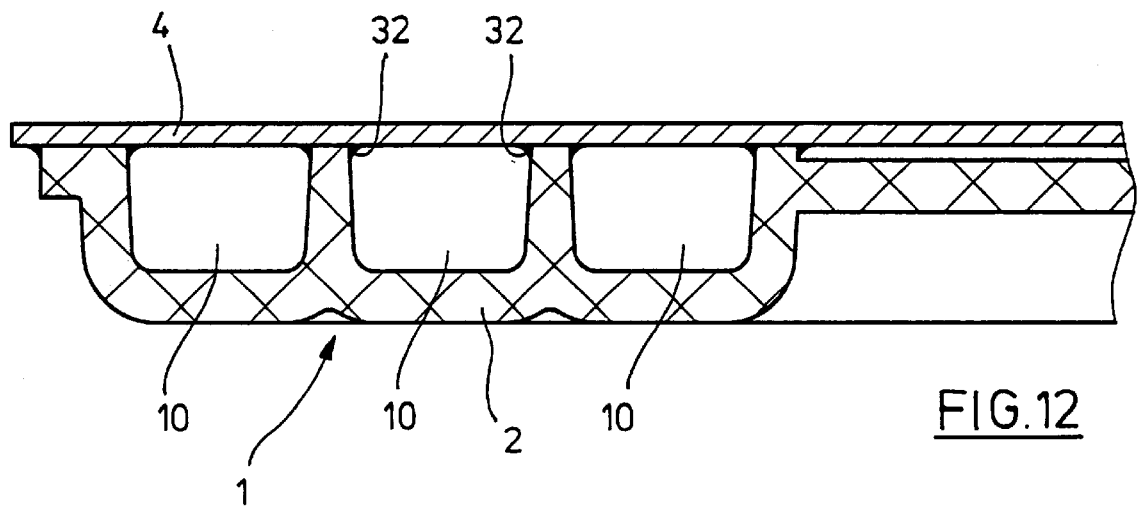

FIG. 11 shows a longitudinal section through a part of the packaging 1' along line S from FIG. 9. When sealing the cover 4, beads 32 form in the upper end area of the wall of the thread duct 10 to the cover 4 as already explained with regard to FIG. 5. For comparison, FIG. 12 shows a longitudinal section through a part of a version which is very similar to the second version according to FIG. 3, and thus corresponds largely to FIG. 5.

The cardboard of the cover 4 has the advantage of absorbing the moisture which penetrates through the outer wrapper over the course of time and keeping it away from the suture material, see above. The same applies to the cardboard for the basis sheet 34. To ensure that, within a sealed outer wrapper, the suture material stored in a packaging 1 or 1' for surgical suture material does not absorb too much moisture before its expiration date, there must be sufficient cardboard inside the outer wrapper. In the embodiment, this is ensured in the second version according to FIG. 3 by a cover which contains cardboard of 370 g/m$^2$. For packaging 1', there is a slightly larger total amount of cardboard in the cover 4 and the basis sheet 34, each of which contains cardboard of 220 g/m$^2$.

Figure 13:
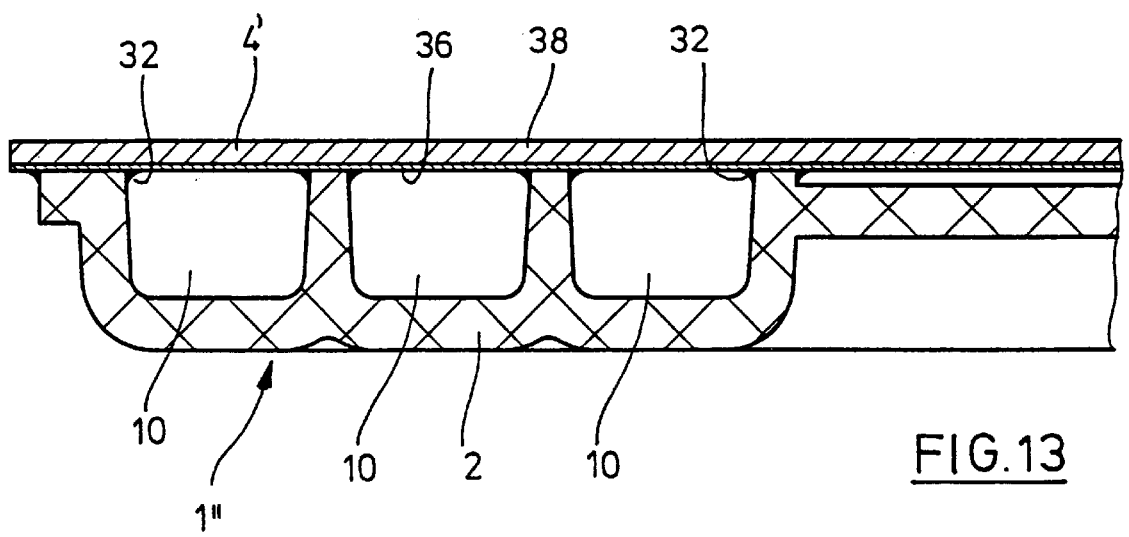

FIG. 13 shows a longitudinal section through a part of a further version of a packaging for surgical suture material, which is designated here with 1". Its base 2 corresponds largely to the bases in the previously mentioned versions, which is why the same reference numbers are used here. The cover, designated here with 4', is constructed differently, however. The cover 4' has a polyolefine fibre tissue (spunbonded polyolefine) on its underside facing the base 2, as sold, for example, by DuPont under the mark "Tyvek". This material is a mixture of polyolefine fibres and paper fibres and is very tear-resistant. It can be sealed onto the base 2 if the base 2 consists of a polyolefine with similar melting point, so that beads 32 form again, see FIG. 13. It is conceivable to use exclusively spunbonded polyolefine as a cover 4'. However, in the embodiment, a piece of cardboard 38 of 370 g/m$^2$ is glued with a hot-melt-type adhesive onto a layer 36 made from spunbonded polyolefine to be able to exploit the ability of the cardboard to absorb moisture.

There are many possibilities for the construction of the cover 4 or 4'. Thus, composite materials or single-layer structures can be used. The use of paper, in particular paper of so-called medical quality, is also conceivable.

I claim:

1. Packaging for surgical sutures, comprising a base having a raised edge and a spiral-like thread duct, which opens at a first end thereof to a thread removal zone defined by a recess in said base located adjacent said first end of said thread duct, said base including a thread tray positioned on an opposite side of said recess from said first end of said thread duct, and a thread holder having a nose extending inwardly from said raised edge of said base above said thread tray; and a cover applied to said base above said thread duct.

2. Packaging according to claim 1, wherein said thread removal zone is formed in a peripheral area of said base.

3. Packaging according to claim 1, wherein said recess extends inwardly from a periphery of said base.

4. Packaging according to claim 1, wherein said thread tray is formed in said base.

5. Packaging according to claim 4, wherein said base has a bottom, a portion of said bottom including said thread tray.

6. Packaging according to claim 1, wherein said thread holder is formed by a part of said base.

7. Packaging according to claim 1, wherein said cover does not cover said thread removal zone.

8. Packaging according to claim 1, wherein said raised edge of said base, in the vicinity of said thread tray, runs traverse to an axis of said thread duct, said axis, in the vicinity of said first end of said thread duct, running in a longitudinal direction of said base.

9. Packaging according to claim 1, wherein said base has a peripheral edge, and said thread duct includes a second end which is spaced inwardly from said peripheral edge of said base.

10. Packaging according to claim 1, wherein said base has a peripheral area and a central area, and said thread duct having a turn in said central area of said base and returning to a second end of said thread duct which is proximate said peripheral area of said base.

11. Packaging according to claim 10, wherein said base and said cover have an opening in the vicinity of said second end of said thread duct.

12. Packaging according to claim 10, wherein said base has an opening in the vicinity of said second end of said thread duct.

13. Packaging according to claim 10, wherein said cover has an opening in the vicinity of said second end of said thread duct.

14. Packaging according to claim 1, wherein said cover is in the form of a flat sheet.

15. Packaging according to claim 14, wherein said cover comprises cardboard.

16. Packaging according to claim 14, wherein said cover comprises paper.

17. Packaging according to claim 14, wherein said cover has an underside facing said base, said underside containing polyethylene.

18. Packaging according to claim 14, wherein said cover has an underside facing said base, said underside containing polypropylene.

19. Packaging according to claim 18, wherein said base has an underside, and said packaging further comprising a warp-resistant sheet applied to said underside of said base.

20. Packaging according to claim 14, wherein said cover has an underside facing said base, said underside containing a spunbonded polyolefine.

21. Packaging according to claim 1, wherein said base is formed as an injection-molded part.

22. Packaging according to claim 21, wherein said base comprises polyethylene.

23. Packaging according to claim 21, wherein said base comprises polypropylene.

24. Packaging according to claim 1, wherein said cover is sealed onto said base.

25. Packaging according to claim 24, wherein said thread duct has an upper end area located adjacent to said cover, said upper end area including a sealing bead formed between said cover and said base.

26. Packaging according to claim 1, wherein said thread tray and said thread holder cooperate so as to form an open compartment therebetween.

27. Packaging according to claim 1, wherein said thread tray and said nose cooperate such that a free end of a surgical thread can be stored therebetween.

28. Packaging for surgical sutures, comprising a base having a peripheral edge, a central area, and a spiral-like thread duct opening at a first end thereof to a thread removal zone defined by a recess in said base located adjacent said first end of said thread duct, said base including a thread tray positioned on an opposite side of said recess from said first end of said thread duct, and said thread duct having a turn in said central area of said base and returning to a second end of said thread duct which is proximate said peripheral edge of said base; and a cover applied to said base above said thread duct.

29. Packaging according to claim 28, wherein said thread removal zone is formed in a peripheral area of said base.

30. Packaging according to claim 28, wherein said recess extends inwardly from a periphery of said base.

31. Packaging according to claim 28, wherein said thread tray is formed in said base.

32. Packaging according to claim 31, wherein said base has a bottom, a portion of said bottom including said thread tray.

33. Packaging according to claim 28, wherein said base includes a thread holder being formed by a part of said base.

34. Packaging according to claim 28, wherein said cover does not cover said thread removal zone.

35. Packaging according to claim 28, wherein said base includes a raised edge, in the vicinity of said thread tray, running traverse to an axis of said thread duct, said axis, in the vicinity of said first end of said thread duct, running in a longitudinal direction of said base.

36. Packaging according to claim 28, wherein said base and said cover have an opening in the vicinity of said second end of said thread duct.

37. Packaging according to claim 28, wherein said base has an opening in the vicinity of said second end of said thread duct.

38. Packaging according to claim 28, wherein said cover has an opening in the vicinity of said second end of said thread duct.

39. Packaging according to claim 28, wherein said cover is in the form of a flat sheet.

40. Packaging according to claim 39, wherein said cover comprises cardboard.

41. Packaging according to claim 39, wherein said cover comprises paper.

42. Packaging according to claim 39, wherein said cover has an underside facing said base, said underside containing polyethylene.

43. Packaging according to claim 39, wherein said cover has an underside facing said base, said underside containing polypropylene.

44. Packaging according to claim 39, wherein said cover has an underside facing said base, said underside containing a spunbonded polyolefine.

45. Packaging according to claim 28, wherein said base is formed as an injection-molded part.

46. Packaging according to claim 45, wherein said base comprises polyethylene.

47. Packaging according to claim 45, wherein said base comprises polypropylene.

48. Packaging according to claim 28, wherein said cover is sealed onto said base.

49. Packaging according to claim 48, wherein said thread duct has an upper end area located adjacent to said cover, said upper end area including a sealing bead formed between said cover and said base.

50. Packaging according to claim 49, wherein said base has an underside, and said packaging further comprising a warp-resistant sheet applied to said underside of said base.

51. Packaging according to claim 28, wherein said thread duct is sized and shaped such that a surgical thread inserted at said first end of said thread duct traverses said turn, and guides toward said second end of said thread duct.

* * * * *